United States Patent
Lacouture et al.

(10) Patent No.: US 11,278,548 B2
(45) Date of Patent: Mar. 22, 2022

(54) METHODS AND COMPOSITIONS FOR REDUCING SIDE EFFECTS IN CHEMOTHERAPEUTIC TREATMENTS

(71) Applicant: Galderma Research and Development, Lausanne (CH)

(72) Inventors: Mario Lacouture, New York, NY (US); Philippe Andres, Peymeinade (FR)

(73) Assignee: Galderma Research and Development, Lausanne (CH)

( * ) Notice: Subject to any disclaimer, the term of this patent is extended or adjusted under 35 U.S.C. 154(b) by 133 days.

(21) Appl. No.: 16/630,989

(22) PCT Filed: Jul. 13, 2018

(86) PCT No.: PCT/US2018/041952
§ 371 (c)(1),
(2) Date: Jan. 14, 2020

(87) PCT Pub. No.: WO2019/014518
PCT Pub. Date: Jan. 17, 2019

(65) Prior Publication Data
US 2020/0222396 A1    Jul. 16, 2020

Related U.S. Application Data

(60) Provisional application No. 62/532,442, filed on Jul. 14, 2017.

(51) Int. Cl.
| *A61K 31/498* | (2006.01) |
| *A61P 17/00* | (2006.01) |
| *A61K 31/137* | (2006.01) |
| *A61K 31/4174* | (2006.01) |
| *A61K 31/7048* | (2006.01) |
| *A61K 45/06* | (2006.01) |

(52) U.S. Cl.
CPC .......... *A61K 31/498* (2013.01); *A61K 31/137* (2013.01); *A61K 31/4174* (2013.01); *A61K 31/7048* (2013.01); *A61P 17/00* (2018.01); *A61K 45/06* (2013.01)

(58) Field of Classification Search
CPC ...... A61K 31/498; A61K 31/137; A61P 17/00
See application file for complete search history.

(56) References Cited

U.S. PATENT DOCUMENTS

| 9,937,117 B2 * | 4/2018 | Andres ................ A61K 31/498 |
| 10,231,908 B2 * | 3/2019 | Andres .................. A61P 17/14 |
| 2015/0313896 A1 | 11/2015 | Bouvier et al. |

FOREIGN PATENT DOCUMENTS

| WO | 2006138691 A1 | 12/2006 |
| WO | 2009032223 A1 | 3/2009 |
| WO | 2012052479 A2 | 4/2012 |
| WO | 2015197524 A1 | 12/2015 |
| WO | 2016128499 A1 | 8/2016 |

OTHER PUBLICATIONS

R. Perez-Soler et al., HER1/EGFR Inhibitor-Associated Rash: Future Directions for Management and Investigation Outcomes from the HER1/EGFR Inhibitor Rash Management Forum, The Oncologist, 10:345-356 (2005).
B. Kaplan et al., Strategies for the management of adverse events associated with mTOR inhibitors, Transplantation Reviews, 28:126-133 (2014).
R. Gutzmer et al., Cutaneous side effects of anti-tumor therapy with BRAF and MEK inhibitors, Hautarzt, 65:582-589 (Jun. 7, 2014).
International Patent Appl'n No. PCT/US2018/041952 (WO 2019/014518), International Search Report, Written Opinion of the International Searching Authority (dated Oct. 30, 2018).

* cited by examiner

*Primary Examiner* — Kevin E Weddington
(74) *Attorney, Agent, or Firm* — Ice Miller LLP

(57) ABSTRACT

A method of preventing or reducing dermatological side effects of the therapeutic agents in a subject without substantial loss in efficacy, where the therapeutic agents would otherwise have significant effects, is described. In particular, the beneficial effects are achieved by using an alpha-2 adrenergic agonist to isolate body areas from pharmacological effects of the therapeutic agents, such as a chemotherapeutic agent, and to prevent or reduce inflammatory processes.

19 Claims, 2 Drawing Sheets

METHODS AND COMPOSITIONS FOR REDUCING SIDE EFFECTS IN CHEMOTHERAPEUTIC TREATMENTS

This application is a section 371 of International Application No. PCT/US18/041952, Jul. 13, 2018, which was published on Jan. 17, 2019 under International Publication No. WO 2019/014518 A1, which claims the benefit of U.S. Provisional Application No. 62/532,442, filed Jul. 14, 2017, the disclosures of all of which are incorporated herein by reference in their entireties.

TECHNICAL FIELD AND BACKGROUND ART

The present invention relates to preventing or reducing dermatological side effects of therapeutic agents in a subject without substantial loss in efficacy, where the therapeutic agents would otherwise have significant side effects. This beneficial effect is achieved by using an alpha-2 adrenergic agonist to isolate body areas from pharmacological effects of the therapeutic agents, such as a chemotherapeutic agent, and to prevent or reduce inflammatory processes.

Side effects are the hallmark of many chemotherapeutic agents which otherwise are effective in reducing tumor size. Among known chemotherapeutic agents, EGFR inhibitors have shown to be active antitumor agents against a variety of solid tumors including but not limited to colorectal carcinoma, non-small cell lung cancer, head and neck cancer and malignant gliomas (Conen et al., 2003; Lage et al., 2003; Lorusso, 2003; Vanhoefer et al., 2004). Clinical benefit defined as relief of symptoms or prolongation of survival has been so far demonstrated with the anti-EGFR antibody cetuximab (Erbitux®) and the EGFR tyrosine kinase (TK) inhibitors gefitinib (Iressa®) and erlotinib)(Tarceva®). Many additional agents belonging to this class are being developed. As of today, FDA approved indications include, e.g., chemorefractory colorectal carcinoma and non-small cell lung cancer, head and neck carcinoma, and pancreatic carcinoma. Many clinical studies using these agents alone or in combination, for refractory or chemo naive patients with a variety of other malignant diseases are in progress.

Undesired adverse effects common to anti-EGFR agents include undesired dermatological side-effects, such as papulopustular rash, usually on the face, upper back and upper torso, which generally develops in a dose-dependent manner. Findings suggest that there is a relationship between the development of rash and response and/or survival. Although most patients only see mild to moderate skin toxicity, clinical benefit of increasing the dose of the various EGFR inhibitors or maintaining their full dose, is expected. Histological data indicate that rash is caused directly by EGFR inhibition in skin.

The above described adverse reactions of EGFR therapy very often lead to drug discontinuation or dose reduction, impairs the quality of life of the patients, puts patients at risk of superinfection and moreover reduces their chances to survive.

Serial biopsies of skin before and after treatment revealed two main reaction patterns: a superficial dermal inflammatory cell infiltrate surrounding hyperkeratotic and ectatic follicular infundibula, and a suppurative superficial folliculitis. Follicular accumulation of neutrophilic granulocytes is considered characteristic for the skin lesion observed after EGFR inhibition. Otherwise, however, little is known about the etiology of this rash, and there are no clear evidence-based management recommendations. Most of the actual management of skin rash resulting from chemotherapies is achieved through treatment rather than preventing the anti-EGFR adverse effects.

Treatment of skin related adverse reactions is currently limited to oral or topical antibiotics, general skin care and hygiene recommendations. The use of other treatment options, such as topical steroids is controversial because of secondary side effects and the higher risk of superinfection in these EGFR-induced rashes, especially on the face. Topical retinoids are not recommended because of the further increase in skin dryness and peeling, and they have never demonstrated efficacy in this indication. Systemic steroids for treatment of severe skin or gastrointestinal adverse reactions are problematic, since they may interfere with EGFR inhibition. Oral antibiotics, although generally well tolerated, can lead to severe gastro-intestinal side effects, drug-drug interaction and bacterial resistance.

Thus, there is an unmet need for novel therapeutic and/or prophylactic strategies to manage adverse skin reactions in patients treated with chemotherapies, such as EGFR inhibitors, especially by preventing or reducing such adverse reactions with a distinct mechanism of action and devoid of additive toxicities.

Therefore, it is the aim of the present invention to provide pharmaceutical compositions for preventing or reducing one or more adverse reactions caused by treatment with a chemotherapeutic agent, such as an EGFR inhibitor.

SUMMARY OF THE INVENTION

The present invention relates to the use of alpha adrenergic agonist, in particular alpha-2 adrenergic agonist, to exclude a skin body part from undesired dermatological side-effects of a chemotherapeutic agent, such as an EGFR inhibitor.

Accordingly, in one general aspect, the invention relates to method of preventing or reducing unwanted dermatological side effects of a chemotherapeutic agent in a skin body part of a subject. The method comprises administering to the subject, preferably topically administering to the skin body part of the subject, an effective amount of a pharmaceutical composition comprising an alpha-2 adrenergic agonist or a pharmaceutically acceptable salt thereof and a pharmaceutically acceptable carrier. The pharmaceutical composition is administered to the subject prior to, simultaneously with, or after the administration of the chemotherapeutic agent to the subject. According to an embodiment of the invention, the method further comprises administering to the subject another pharmaceutical active ingredient. Preferably, the other pharmaceutical active ingredient is an avermetin, such as an ivermectin or an emamectin, and is topically administering to the skin body part together with the alpha-2 adrenergic agonist in one or separate compositions, or the alpha-2 adrenergic agonist and the avermetin are topically applied to the skin body part sequentially.

In another general aspect, the invention relates to the use of an alpha adrenergic agonist, in particular an alpha-2 adrenergic agonist, for the prevention or reduction of undesired dermatological side-effects of a chemotherapy, such as an EGFR treatment, in a subject in need thereof, in particular for the prevention or reduction of rash caused by the chemotherapy.

According to an embodiment of the invention, the subject in need of a treatment of the invention is undergoing, or is enrolled to undergo a chemotherapy, such as an anti-EGFR treatment. The method comprises administering an effective amount of an alpha-2 adrenergic agonist to the subject, preferably topically administering an effective amount of an alpha-2 adrenergic agonist to a skin body part of the subject, more preferably, prior to administering the chemotherapeutic agent to the subject.

The invention also relates to the use of an alpha-2 adrenergic agonist for the preparation of a pharmaceutical composition for preventing or reducing an undesired dermatological side-effect in an individual undergoing, or enrolled to undergo a chemotherapy, such as an anti-EGFR treatment.

In a further aspect, the invention relates to a composition suitable for use in a method of the invention, comprising an alpha-2 adrenergic agonist, wherein said alpha-2 adrenergic agonist is present in an amount sufficient to reduce and/or prevent one or more undesired dermatological side-effects of the chemotherapy, such as the anti-EGFR agent.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 3A shows a grade 2 rash at baseline, and FIG. 3B shows a grade 1 rash in 2 month follow up.

DETAILED DESCRIPTION OF THE INVENTION

Definitions

Figure 1:
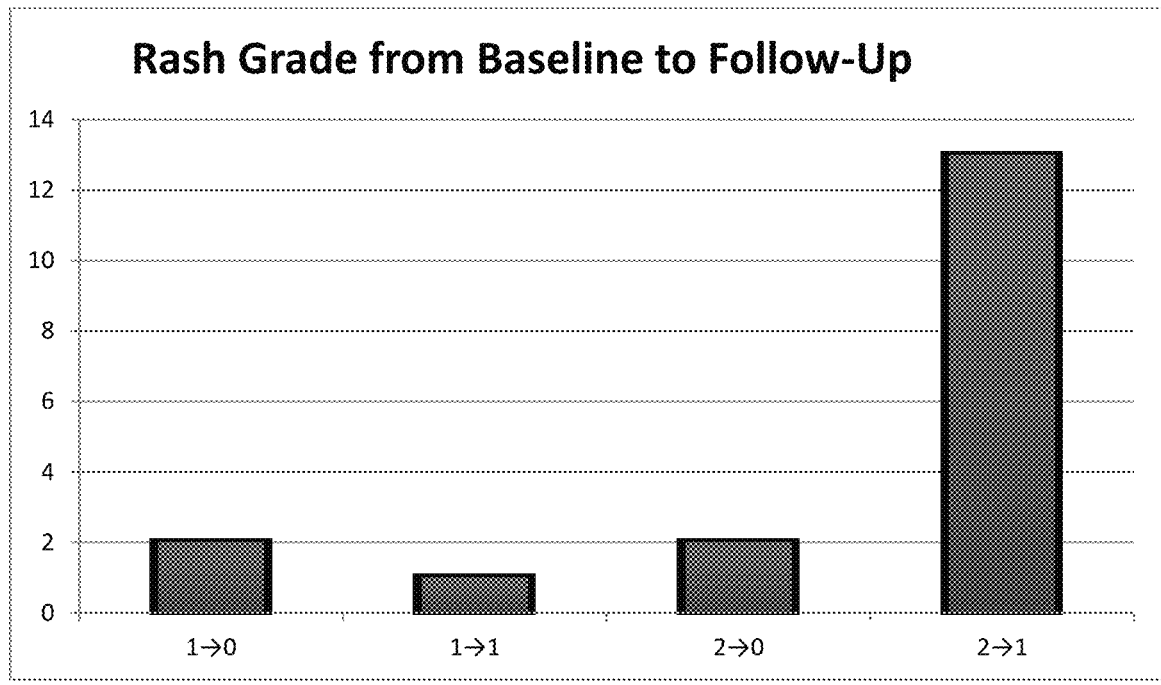
FIG. 1 shows the bar graph of Acneiform rash (e.g., rash grade) outcome of patients treated with brimonidine gel.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural references unless the context clearly dictates otherwise.

As used herein, the term "skin body part" refers to an external location on the human skin that can be defined either by surface or location on the body. A non-limiting list of "skin body part" includes, e.g., scalp, face, neck, shoulders, back (upper and lower), torso, belly, genitals, arm, forearm, leg(s), hand(s) and foot/feet more preferably hand(s), foot/feet, fingers, toes, or the face.

As used herein, the term "excluding a skin body part" refers to excluding the skin body part from a pharmacological activity of a chemotherapeutic agent, more preferably, denying, reducing or limiting access of the chemotherapeutic agent to the blood stream of the specific body surface.

As used herein, the phrase "unwanted dermatological side effects" refers to any unwanted reactions of a skin body part to a drug therapy, such as a chemotherapy (e.g., a treatment with an anti-EGFR, an MEK inhibitor, an mTOR inhibitor, or a combination thereof). Examples of such unwanted reactions include, but are not limited to, rash, such as papulopustular rash, dry skin, flushing, hyperpigmentation, unwanted nail changes, and photosensitivity. The "unwanted dermatological side effects" usually develop on the face, upper back and upper torso, but can also occur on other body part. The side effects generally develop in a dose-dependent manner, but can also be dose-independent.

As used herein, the term "chemotherapy" refers to a type of cancer treatment that uses one or more anti-cancer drugs (chemotherapeutic agents) to kill cancer cells. Chemotherapy may be given with a curative intent, or it may aim to prolong life or to reduce symptoms.

As used herein, the term "chemotherapeutic agent" or "chemotherapeutic compound" refers to any agent that can be used to treat a disease or disorder of a subject. Preferably, a "chemotherapeutic agent" or "chemotherapeutic compound" is used to treat a tumor or cancer. Conventional chemotherapy uses non-specific cytotoxic drugs to inhibit cell division (mitosis). Hormone therapy is one type of cancer treatment that inhibits growth-promoting signals from classic endocrine hormones, primarily estrogens for breast cancer and androgens for prostate cancer. By contrast, targeted therapy is another type of cancer treatment that inhibits growth-signals like those associated with receptor tyrosine kinases.

Based on their principal mechanism of action, conventional chemotherapeutics can be broadly subdivided into: 1) alkylating agents; 2) antimetabolites; 3) topoisomerase inhibitors; 4) microtubular poisons; and 5) cytotoxic antibiotics.

Hormone therapy falls into two broad groups, those that block the body's ability to produce hormones and those that interfere with how hormones behave in the body.

Most chemotherapeutic agents in targeted therapy are either small-molecule drugs or monoclonal antibodies. Small-molecule drugs are small enough to enter cells easily, so they are used for targets that are inside cells. Monoclonal antibodies are drugs that attach to specific targets on the outer surface of cancer cells. Examples of chemotherapeutic agents for target therapy include, but are not limited to an anti-EGFR compound, an MEK inhibitor and an mTOR inhibitor.

As used herein, the term "anti-EGFR compound" refers to an active ingredient having an anti-EGFR pharmacological activity. In a preferred embodiment, the compound having an anti-EGFR activity is selected from the group consisting of cetuximab, gefitinib, erlotinib, necitumumab, neratinib, panitumumab, vandetanib, osimertinib, and lapatinib.

As used herein, the term "MEK inhibitor" refers to an active ingredient that inhibits the mitogen-activated protein kinase kinase enzymes MEK1 and/or MEK2. In a preferred embodiment, the MEK inhibitor compound is selected from the group consisting of trametinib, selumetinib, binimetinib, refametinib, pimasertib, and cobimetinib.

As used herein, the term "mTOR inhibitor" refers to an active ingredient that inhibits the mechanistic target of rapamycin (mTOR). In a preferred embodiment, the mTOR inhibitor compound is selected from the group consisting of rapamycin (sirolimus), temsirolimus, everomilus, ridaforolimus, dactolisib (NVP-BEZ235), GSK2126458, XL765, AZD8055, sapanisertib (INK128), OSI027, and rapalink-1.

As used herein, the term "alpha adrenergic receptor" refers to any of an alpha 1 and alpha 2 adrenergic receptors that were distinguished from each other in the 1970's. During the same decade, alpha 2 adrenergic receptors were found to occur on vascular smooth muscles and exhibit mediation of vasoconstrictor response (Docherty, "Subtypes of functional α1- and α2-adrenoceptors," *European Journal of Pharmacology,* 1998, 361: 1-15). Thus, molecules exhibiting alpha adrenergic agonism, advantageously alpha 2 adrenergic agonism, possess peripheral vasoconstrictive activity. Among the alpha receptors, the agonist can be an agonist of both alpha 1 and alpha 2 receptors, or can be specific for alpha 1 or alpha 2. Preferably, the chosen molecule displays more affinity for the alpha 2 than for the alpha 1 receptor, and will generally be named, in the rest of the application, "an alpha 2 adrenergic receptor agonist."

Agonists of the alpha-2 adrenoceptors have been used therapeutically for a number of conditions including hypertension, congestive heart failure, angina pectoris, spasticity, glaucoma, diarrhea, and for the suppression of opiate withdrawal symptoms (Heible and Ruffolo, "Therapeutic Applications of Agents Interacting with α-Adrenoceptors," in *Progress in Basic and Clinical Pharmacology,* Vol. 8, p. 180-206, P. Lomax and E. S. Vesell Ed., Karger, 1991). Adrenoceptor agonists such as clonidine have been primarily used orally, though a patch formulation is known. The alpha-2 agonists are known to mediate vasoconstriction both in the core and periphery of a patient. In particular alpha-2 adrenoceptor agonists are known to cause vasoconstriction of peripheral arterioles, in response to stimulation due to cold or stress.

The most preferred compound is (5-bromo-quinoxalin-6-yl)-(4, 5-dihydro-IH-imidazol-2-yl)-amine (commonly referred to as brimonidine) and pharmaceutically acceptable salts thereof, particularly the tartrate salt. Other adrenoceptor agonists useful in the invention include naphazoline, tetra-hydrozaline, oxymetazoline, xylometazoline, epinephrine, norepinephrine, phenylephrine and methoxamine and their pharmaceutically acceptable salts.

As used herein, the term "brimonidine" refers to the compound (5-bromo-quinoxalin-6-yl)-(4,5-dihydro-1H-imidazol-2-yl)-amine having the structure of Formula (I):

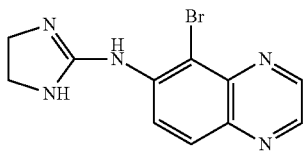 [SMILES: Brc1c(NC2=NCCN2)ccc2nccnc12]

and any pharmaceutically acceptable salt of the compound, such as brimonidine tartrate.

The phrase "pharmaceutically acceptable salt(s)," as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts.

For a review on pharmaceutically acceptable salts see Berge et al., 66 *J. Pharm. Sci.* 1-19 (1977), incorporated herein by reference.

As used herein, the term "composition" is intended to encompass a product comprising the specified ingredient in the specified amount, as well as any product which results, directly or indirectly, from combinations of the specified ingredient in the specified amount.

The term "topically administrable composition," a "topical composition," or a "topical formulation," as used herein, means any formulation or composition which is pharmaceutically and/or cosmetically acceptable for topical delivery of the specified compounds according to embodiments of the invention. Exemplary forms of formulation that can be used for topical administration in embodiments of the present invention include, but are not limited to, sprays, mists, aerosols, solutions, lotions, gels, creams, ointments, pastes, unguents, emulsions and suspensions.

The term "topically administrable composition" as used herein, also encompasses locally applied and locally acting formulations such as formulations for use with implants, injections, or patches.

As used herein, the term "subject" means any animal, preferably a mammal, most preferably a human, to whom will be or has been administered compounds or topical formulations according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, "prevention" or "preventing" refers to a reduction of the risk of acquiring a given disease or disorder. In a preferred mode of the embodiment, the specified compounds are administered as a preventative measure to a subject having a predisposition to a disease or disorder even though symptoms of the disease or disorder are absent or minimal.

Embodiments of the Invention

The invention relates to a method of preventing or reducing undesired dermatological side-effects of a chemotherapeutic compound and symptoms associated therewith in a subject in need thereof. The method comprises administering to the subject, preferably topically administering to a skin body part of the subject, a pharmaceutical composition comprising an alpha-2 adrenergic receptor agonist or a pharmaceutically acceptable salt thereof, and a pharmaceutically acceptable carrier before, during, and/or after the course of the chemotherapy.

In a preferred embodiment of the invention, the chemotherapeutic compound is an anti-EGFR compound, an MEK inhibitor compound, a mTOR inhibitor compound, or a combination thereof.

In a preferred embodiment of the invention, the alpha-2 adrenergic receptor agonist is brimonidine or one of its pharmaceutically acceptable salt, such as brimonidine tartrate.

The undesired side-effect(s) or adverse effect(s) of a chemotherapy, such as an anti-EGFR treatment, that are prevented or reduced by administration of the alpha adrenergic receptor agonist, are of any type of dermatological side-effect of such treatment, such as rash, folliculitis, dry skin or nail changes, e.g. paronychia. However, in a preferred embodiment, the undesired dermatological side-effect that is reduced or prevented by the alpha adrenergic receptor agonist is rash, such as follicular rash.

Rash can be quantified using methods known in the art in view of the present disclosure. For example, a reduction in rash, e.g. of 10%, when used herein indicates that is a statistically significant reduction of 10% in the total score of a representative population, as compared to the same treatment with the chemotherapy (such as an anti-EGFR agent) alone, i.e. without administration of an alpha adrenergic receptor agonist. The reduction can be the result of prevention and/or treatment, preferably through prevention.

In a preferred embodiment of the method or use of the invention, the rash is reduced by at least 10%, such as at least 20%, e.g. at least 30%, such as at least 40%, e.g. at least 50%, such as at least 60%, e.g. at least 70%, such as at least 80%, e.g. at least 90%, such as least 95%

Another embodiment of the present invention relates to a method of limiting the progression of undesired dermatological side-effects of EGFR treatment in a subject by excluding a skin body part, which comprises topically administering to the skin body part a composition comprising a therapeutically effective amount of an alpha 2 adrenergic receptor agonist and a pharmaceutically acceptable carrier. While not wishing to be bound by theories, it is believed that, due to its vasoconstriction function, the effective amount of alpha-2 adrenergic receptor agonist excludes the skin body part from the pharmacological activity of the chemotherapeutic agent, for example, by denying, reducing or limiting access of the chemotherapeutic agent to the blood stream of the specific body surface, and such exclusion contributes to the prevention or reduction of the undesired dermatological side-effects of the chemotherapeutic compound. Narrowing the blood vessels does also limit the inflammatory processes such as leukocyte recruitment and subsequent cytokine production and release.

According to a preferred embodiment of the present invention, a method of preventing or limiting the progression of an undesired dermatological side-effect of chemotherapeutic agent, such as an anti-EGFR compound, an MEK inhibitor, or an mTOR inhibitor, in a subject, comprises administering to the subject, preferably topically administering to a skin body part of the subject, an effective amount of a pharmaceutical composition comprising brimonidine or a pharmaceutically acceptable salt thereof, and a pharmaceutically acceptable carrier.

More preferably the present invention relates to a method of preventing or limiting the progression of skin rash associated with a chemotherapeutic agent treatment in a subject in need thereof. The method comprises topically administering to the subject an effective amount of a composition comprising brimonidine or a pharmaceutically acceptable salt thereof and a pharmaceutically acceptable carrier.

According to embodiments of the invention, the method further comprises administering to the subject one or more additional active pharmaceutical ingredient for reducing or treating the undesired dermatological side-effect of chemotherapeutic agent. The additional active pharmaceutical ingredients can be administered together with the alpha-2 adrenergic receptor agonist in the same pharmaceutical composition or in a separate pharmaceutical composition. The additional active pharmaceutical ingredients and the alpha-2 adrenergic receptor agonist can also be administered to the subject sequentially. Preferably, the additional active pharmaceutical ingredient is an avermectin, such as an ivermectin or an emamectin. More preferably, the avermectin is topically administered to the subject with the alpha-2 adrenergic receptor agonist in one pharmaceutical composition.

Dosage Regimens

In the method and use of the invention, the alpha adrenergic receptor agonist are given in an effective amount, i.e. in an amount effective, at dosages and for periods of time necessary, to achieve a desired result.

A therapeutically effective amount can vary according to factors such as the disease state, age, sex, and weight of the individual, and the ability of the agent to elicit a desired response in the individual.

To treat or prevent undesired dermatological side-effects of chemotherapeutic treatments or a symptom associated therewith, the topically administrable compositions of the invention can be topically applied directly to the skin body part to be excluded from chemotherapeutic treatment in any conventional manner known in the art, e.g., by dropper, applicator stick, or cotton swab, as a mist via an aerosol applicator, via an intradermal or transdermal patch, or by simply spreading a formulation of the invention onto the affected area with fingers, a sponge, a pad, or wipes.

Generally the amount of a topical formulation of the invention applied to the affected skin area ranges from about 0.0001 g/cm$^2$ of skin surface area to about 0.05 g/cm$^2$, preferably, 0.002 g/cm$^2$ to about 0.005 g/cm$^2$ of skin surface area.

In various aspects, an application of a topical composition can noticeably prevent an undesired dermatological side-effects of chemotherapeutic treatments within and can be maximally effective at about 30 minutes after application, and the ameliorative effects can last up to about 2 hours, up to about 4 hours, up to about 8 hours, up to about 12 hours, up to about 18 hours, or up to about 24 hours, or longer.

Accordingly, in some aspects, a composition can be topically applied to skin body part at a site to be excluded from chemotherapeutic treatment symptoms once per day, twice per day, or three or more times per day.

Formulation, Additives and Mode-of-Administration

In one embodiment, the alpha adrenergic receptor agonist of the invention are preventively delivered to a skin body part in a pharmaceutically acceptable topical carrier. As used herein, a "pharmaceutically acceptable topical carrier" is any pharmaceutically acceptable carrier that can be applied to the skin surface for topical, dermal, intradermal, or transdermal delivery of a pharmaceutical or medicament. The combination of a pharmaceutically acceptable topical carrier and a compound of the invention is termed a topical formulation of the invention.

In view of the present disclosure, the pharmaceutical compositions and agents can be formulated with pharmaceutically acceptable carriers or diluents as well as any other known adjuvants and excipients in accordance with conventional techniques, such as those disclosed in Remington: *The Science and Practice of Pharmacy,* 19th Edition, Gennaro, Ed., Mack Publishing Co., Easton, Pa., 1995.

The pharmaceutically acceptable carriers or diluents as well as any other known adjuvants and excipients should be suitable for the chosen composition of the present invention and the chosen mode of administration. Suitability for carriers and other components of pharmaceutical compositions is determined based on the lack of significant negative impact on the desired biological properties of the chosen compound or pharmaceutical composition of the present invention, e.g., less than a substantial impact (10% or less relative inhibition, 5% or less relative inhibition, etc.) on the desired biological properties of an alpha agonist used in the present invention.

A pharmaceutical composition of the present invention can also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient.

The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a composition in vivo and in vitro are well known in the art and may be selected by those of ordinary skill in the art. Preferably, the pharmaceutical composition containing an alpha-2 adrenergic agonist is administered to a skin body part of interest by topical administration.

Brimonidine and its pharmaceutically acceptable salts are preferred embodiments of the invention. Preferably, the active ingredient of the composition is brimonidine tartrate.

In an embodiment of the present invention, the topically administrable composition comprises about 0.1%, 0.2%, 0.3%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or 10.0%, by weight of an alpha-2 adrenergic agonist, preferably brimonidine, such as brimonidine tartrate.

In another embodiment of the present invention, the topically administrable composition comprises about 0.15%, about 0.2%, about 0.25%, about 0.3%, about 0.35%, about 0.4%, about 0.45%, about 0.5%, about 0.55% or about 0.6%, by weight of an alpha-2 adrenergic agonist, preferably brimonidine, such as brimonidine tartrate.

In a preferred embodiment, the topical composition comprises about 0.5% by weight of an alpha-2 adrenergic agonist, preferably brimonidine, such as about 0.5% by weight of brimonidine tartrate.

In one embodiment of the invention, the topical composition is contained within one suitable container, such as a dropper, a jar, or a tube with a suitable small orifice size, such as an extended tip tube, made of any pharmaceutically suitable material. The topical formulations according to embodiments of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332. Optionally, an applicator can be provided in or attached to the container, or separately from the container.

In one embodiment of the invention, the instructions are, for example, a pamphlet or package label. The instructions explain how to administer topical formulations of the invention, in an amount and for a period of time sufficient to provide a safe and effective treatment of erythema or a symptom associated therewith. Preferably, the instructions include, for example, the dosage and administration instructions, the topical formulation's composition, the clinical pharmacology, drug resistance, pharmacokinetics, absorption, bioavailability, and contraindications.

Another aspect of the present invention relates to a topical gel composition for preventing or reducing unwanted dermatological side effects in a skin body part due to administration of a chemotherapeutic agent in a subject. The topical gel composition comprises:

about 0.1% (w/w) to about 10.0% (w/w) an alpha-2 adrenergic agonist, preferably brimonidine, such as brimonidine tartrate;

about 0.20% (w/w) to about 4.0% (w/w) gelling agent; and about 5.0% (w/w) to about 30.0% (w/w) at least one polyol.

According to an embodiment of the invention, the topical administration of the topical gel composition to a skin body part excludes the skin body part from a pharmacological activity of a chemotherapeutic agent, thereby preventing unwanted dermatological side effects in the skin body part due to administration of a chemotherapeutic agent.

The topically administrable composition are prepared by mixing a pharmaceutically acceptable carrier with the safe and effective amount of an alpha-2 adrenergic agonist, such as brimonidine, according to known methods in the art, for example, methods provided by standard reference texts such as, REMINGTON: THE SCIENCE AND PRACTICE OF PHARMACY 1577-1591, 1672-1673, 866-885(Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In a preferred embodiment, the topical gel composition comprises about 0.1% to about 0.6% by weight of an alpha-2 adrenergic agonist, preferably brimonidine, more preferably, 0.5% by weight of brimonidine tartrate.

Suitable gelling agents known in the art, including those used in the two-phase or single-phase gel systems, can be used in the present invention. Some examples of suitable gelling agents are disclosed in REMINGTON: THE SCIENCE AND PRACTICE OF PHARMACY 1517-1518 (Alfonso R. Gennaro ed. 19th ed. 1995), which is hereby incorporated herein by reference. The gelling agents used in embodiments of the present invention, include, but are not limited to, one or more hydrophilic and hydroalcoholic gelling agents used in the cosmetic and pharmaceutical industries. Preferably, the hydrophilic or hydroalcoholic gelling agent comprises "CARBOPOL (Registered trademark)" (B.F. Goodrich, Cleveland, Ohio), "HYPAN (Registered trademark)" (Kingston Technologies, Dayton, N.J.), "NATROSOL (Registered trademark)" (Aqualon, Wilmington, Del.), "KLUCEL (Registered trademark)" (Aqualon, Wilmington, Del.), or "STABILEZE (Registered trademark)" (ISP Technologies, Wayne, N.J.). The preferred compositional weight percent range for "CARBOPOL (Registered trademark)" is between about 0.5% to about 2%, while the preferred weight percent range for "NATROLSOL (Registered trademark)" and "KLUCEL (Registered trademark)" is between about 0.5% to about 4%. The preferred compositional weight percent range for both "HYPAN (Registered trademark)" and "STABILEZE (Registered trademark)" is between 0.5% to about 4%. Other preferred gelling agents include hydroxyethylcellulose, cellulose gum, MVE/MA decadiene crosspolymer, PVM/MA copolymer, glycerine polyacrylate, or a combination thereof.

Examples of carbomers that can be used in the present invention include, but are not limited to, Carbomer 910, 934P, 940, 941, 980 and 1342, and Carbopol (Registered trademark) 974P and Carbopol (Registered trademark) 980. Preferably, the carbomer is Carbomer 934P or Carbopol (Registered trademark) 974P, and Carbopol (Registered trademark) 980.

According to embodiments of the present invention, the amount of the carbomer in the composition is about 0.5%, 0.6%, 0.7%, 0.8%, 0.85%, 0.95%, 1.05%, 1.15%, 1.25%, 1.35%, 1.45%, 1.5%, 1.6%, 1.7%, 1.8%, 1.9% or 2.0% (w/w).

The following examples are offered to illustrate, but not to limit the claimed invention.

EXAMPLE 1

Formulations

Exemplary formulations useful in the present invention are prepared using methods known in the art, e.g., by mixing the following ingredients at the specified concentrations:

Formulation 1

| Ingredient | % relative to the total weight of the composition |
|---|---|
| Brimonidine tartrate | 0.20% |
| Ivermectin | 1.00% |
| EDTA | 0.1% |
| Polysorbate 80 | 8.0% |
| Propylene glycol | 20.0% |
| Benzyl alcohol | 3% |
| Water | QS |
| TOTAL | 100% |

Formulation 2

| Ingredient | % relative to the total weight of the composition |
|---|---|
| Brimonidine tartrate | 0.3% |
| Emamectin | 0.5% |
| Codex petroleum jelly | 56.0% |
| Liquid petroleum jelly | 43.0% |

Formulation 3

| Ingredient | % relative to the total weight of the composition |
|---|---|
| Oxymetazoline hydrochloride | 0.20% |
| Ivermectin | 1.4% |
| Glycerol | 4.0% |
| Steareth-2 | 1.0% |
| Steareth-21 | 2.0% |
| Aluminum magnesium silicate/titanium dioxide/silica | 1.0% |
| Methyl para-hydroxybenzoate | 0.2% |
| Propyl para-hydroxybenzoate | 0.1% |
| Disodium EDTA | 0.05% |
| Citric acid monohydrate | 0.05% |
| Isopropyl palmitate | 4.0% |
| Glyceryl/PEG 100 stearate | 2.0% |
| Self-emulsifiable wax | 1.0 |
| Palmitostearic acid | 2.0% |
| Dimethicone 200-350 cS | 0.5% |
| Propylene glycol | 4.0% |
| Glyceryl triacetate | 1.0% |
| Phenoxyethanol | 0.5% |
| 10% sodium hydroxide | qs pH |
| Water | QS |
| TOTAL | 100% |

Formulation 4

| Ingredient | % relative to the total weight of the composition [% (w/w)] |
|---|---|
| Brimonidine tartrate | 0.15% |
| Ivermectin | 0.03% |
| Polysorbate 80 | 2.00% |
| Benzalkonium chloride | 0.05% |
| EDTA | 0.05% |
| Buffer system | pH 6.3 |
| Water | QS |
| TOTAL | 100% |

Additional Formulations

| Ingredient | % (w/w) | % (w/w) | % (w/w) |
|---|---|---|---|
| Brimonidine tartrate | 0.3-1% | 0.6-3.0% | 3.0-10% |
| Carbomer 934P | 1.25% | 1.0% | 1.5% |
| Methylparaben | 0.2% | 0.15% | 0.20% |
| Phenoxyethanol | 0.4% | 0.35% | 0.4% |
| Glycerol | 5.5% | 10% | 15% |
| Kowet titanium dioxide | 0.0625% | 0.0725% | 0.0825% |
| Propylene glycol | 5.5% | 10% | 15% |
| DI Water | QS | QS | QS |
| TOTAL | 100% | 100% | 100% |

EXAMPLE 2

A retrospective analysis was conducted on epidermal growth factor receptor-inhibition (EGFRI)-treated patients receiving brimonidine gel for acneiform rash. The characteristics of these patients were reviewed in 2 centers. Demographics, primary tumor, anticancer therapy agent, and treatment of acneiform rash were summarized. Documentation on grading of rash using the Common Terminology Criteria for Adverse Events v4.0 (CTCAE) (Chen, et al., Journal of the American Academy of Dermatology, 2012, 67(5):1025-39) was gathered. Data was reported using descriptive statistics.

Materials and Methods

Figure 2:
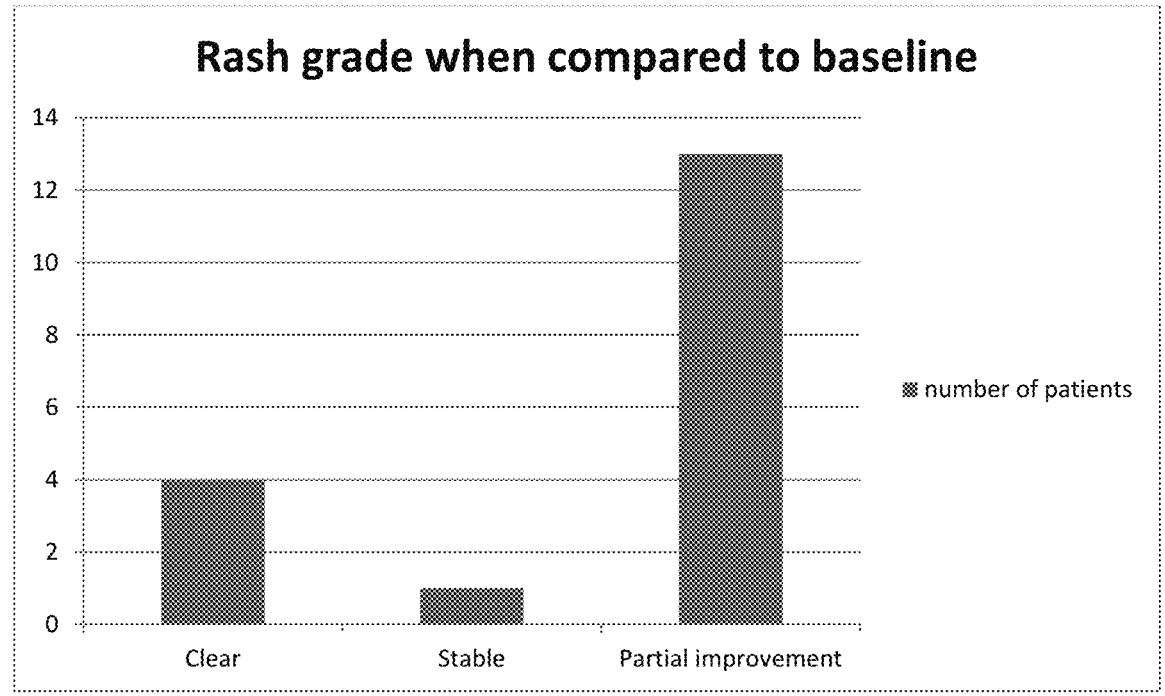
FIG. 2 shows the bar of Aceniform rash outcome (e.g., clear, stable, or partial improvement) of patients treated with brimonidine gel when compared to baseline.
Figure 3A:
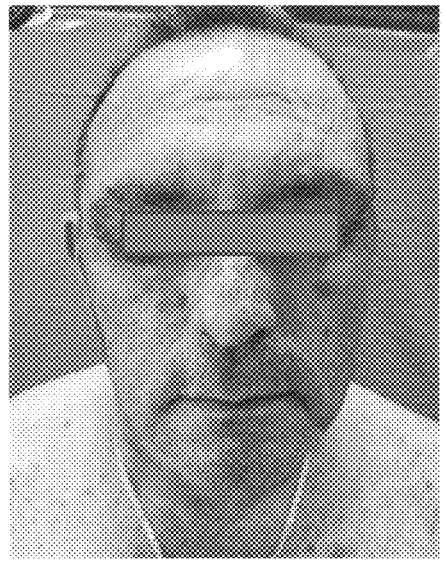
FIGS. 3A-3B show a patient with metastatic colorectal cancer treated on panitumumab treated with brimonidine gel.
Figure 3B:
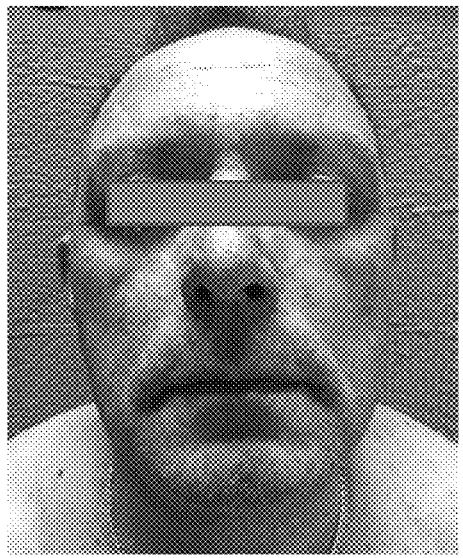

A total of 18 patients were identified, with a median age of 53 years, predominantly male patients (n=10, 55.6%), and most presented with a solid tumor (n=16, 88.9%), primarily lung cancer (n=5, 27.8%). Grade ≥2 rash at presentation (Common Terminology Criteria for Adverse Events v4.0) was observed in 83.3% (n=15) of patients. Causal agents were monoclonal antibodies (n=101, 34%) and small molecules (n=101, 34%). Patients on brimonidine were followed for 12 to 24 weeks Results FIG. 1 and FIG. 2 demonstrated that the majority of treated patients had a decrease in rash severity (n=17, 94%), and did not require dose modification of anticancer therapies. FIGS. 3A-3B compared the rash in a patient between the baseline and 2 month follow up. Adverse events to brimonidine were not reported.

This data demonstrates an improvement in acneiform rash in all patients. It is noted that 83% of patients were also receiving systemic antibiotics (72%) and topical antibiotics or corticosteroids (83%).

This analysis demonstrated that the addition of brimonidine gel had a therapeutic benefit for the acneiform rash from targeted cancer therapies. In addition, no adverse events to brimonidine were reported by patients reported herein. All of which suggested that the addition of brimonidine can improve quality of life and prevent dosing interruptions or decreases in the dosing of anticancer agents.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preventing or reducing a rash in a skin body part of a human subject induced by a chemotherapeutic agent, comprising administering to the subject an effective amount of a pharmaceutical composition comprising an alpha-2 adrenergic agonist having more affinity for an alpha-2 adrenoreceptor than for an alpha-1 adrenoreceptor, or a pharmaceutically acceptable salt thereof, and a pharmaceutically acceptable carrier.

2. The method according to claim 1, wherein the skin body part is selected from the group consisting of scalp, face, neck, shoulders, back (upper and lower), torso, belly, genitals, arms, forearms, legs, hands and feet.

3. The method according to claim 1, wherein the skin body part is selected from the group consisting of scalp, face, upper back, and upper torso.

4. The method according to claim 1, wherein the chemotherapeutic agent is selected from a group consisting of an anti-EGFR compound, an MEK inhibitor compound, and an mTOR inhibitor compound.

5. The method according to claim 1, wherein the chemotherapeutic agent is selected from the group consisting of cetuximab, gefitinib, erlotinib, panitumumab, lapatinib, trametinib, selumetinib, binimetinib, and cobimetinib.

6. The method of claim 1, wherein the pharmaceutical composition further comprises an avermectin.

7. The method of claim 6, wherein the avermectin is emamectin or ivermectin.

8. The method of claim 1, wherein the pharmaceutical composition is topically administered to the skin body part of the human subject.

9. The method of claim 1, wherein the rash is an acneiform rash.

10. The method of claim 1, wherein the rash is a follicular rash.

11. The method of claim 1, wherein the pharmaceutical composition is administered before administration of the chemotherapeutic agent.

12. The method of claim 1, wherein the pharmaceutical composition is administered during administration of the chemotherapeutic agent.

13. The method of claim 1, wherein the pharmaceutically acceptable carrier comprises a gelling agent and a polyol.

14. The method of claim 1, wherein administration of the pharmaceutical composition reduces dosing interruptions of the chemotherapeutic agent for at least 12 weeks.

15. The method of claim 1, further comprising administration of the pharmaceutical composition without the administration of an antibiotic or a corticosteroid to the skin body part of the human subject for at least 12 weeks.

16. A method of preventing or reducing a rash in a skin body part of a human subject induced by a chemotherapeutic agent, comprising administering to the human subject an effective amount of a pharmaceutical composition comprising brimonidine or a pharmaceutically acceptable salt thereof, and a pharmaceutically acceptable carrier.

17. The method of claim 16, wherein the pharmaceutically acceptable salt is brimonidine tartrate.

18. The method of claim 17, wherein the brimonidine tartrate is about 0.1% (w/w) to about 10.0% (w/w) of the pharmaceutical composition.

19. The method of claim 16, wherein the pharmaceutical composition is a gel composition comprising about 0.1% to about 0.6% by weight of brimonidine or a pharmaceutically acceptable salt thereof.

* * * * *